United States Patent [19]

Parks

[11] Patent Number: 4,678,756
[45] Date of Patent: Jul. 7, 1987

[54] CHEMILUMINESCENT SULFUR DETECTION APPARATUS AND METHOD

[75] Inventor: Robert E. Parks, Houston, Tex.

[73] Assignee: Antek Instruments, Inc., Houston, Tex.

[21] Appl. No.: 386,712

[22] Filed: Jun. 9, 1982

Related U.S. Application Data

[62] Division of Ser. No. 232,891, Feb. 9, 1981, Pat. No. 4,352,779.

[51] Int. Cl.$^4$ .............................................. G01N 21/76
[52] U.S. Cl. .................................... 436/123; 436/159; 436/172
[58] Field of Search .................. 422/52; 436/172, 119, 436/120, 121, 122, 123, 159, 160

[56] References Cited

U.S. PATENT DOCUMENTS

| | | | |
|---|---|---|---|
| 3,540,851 | 11/1970 | Vree et al. | 23/232 E |
| 3,700,896 | 10/1972 | Anderson et al. | 422/52 |
| 3,749,929 | 7/1973 | Wooten et al. | 23/232 E |
| 3,756,781 | 9/1973 | Kimbell | 23/230 PC |
| 3,838,969 | 10/1974 | Dugan | 230/230 PC |
| 3,877,819 | 4/1975 | Waas | 23/230 PC |
| 3,973,914 | 8/1976 | Van Heusden | 422/52 |
| 3,984,688 | 10/1976 | Von Bargen et al. | 250/361 C |
| 4,018,562 | 4/1977 | Parks et al. | 422/52 |
| 4,077,774 | 3/1978 | Neti et al. | 23/232 E |
| 4,097,239 | 6/1978 | Patterson | 23/232 R |
| 4,193,963 | 3/1980 | Bruening et al. | 422/52 |
| 4,236,895 | 12/1980 | Stahl | 422/52 |
| 4,238,198 | 12/1980 | Swaine et al. | 422/52 |

OTHER PUBLICATIONS

Ogino et al., Chemical Abstracts, vol. 85, 1976, No. 85:181620a.
Turner, Chemical Abstracts, vol. 86, 1977, No. 86:110538q.

Primary Examiner—Michael S. Marcus

[57] ABSTRACT

In the illustrated and preferred embodiment of this disclosure, a chemiluminescent sulfur detector, both method and apparatus, for detecting bonded sulfur in compounds is disclosed. The illustrated and preferred embodiment, being provided with a discrete sample, passes the sample through a first furnace in the presence of a carrier of inert gas and is exposed to a suitable granulated metal oxide, such as copper oxide or vanadium pentoxide, resulting in oxidation of the sulfur compound. The sample is then passed through a second furnace comingled with elemental hydrogen, there being a conversion of sulfur oxides to hydrogen sulfide. The output of the second furnace is dried. The hydrogen sulfide, along with the inert carrier gas, is introduced into a reaction chamber and is mixed with ozone. A chemiluminescent reaction occurs in the chamber, and the resulting light emission is measured photoelectrically by either a photomultiplier tube or photodiode. The output from the photomultiplier tube is connected to a summing circuit, and the summation represents the measure of sulfur in the specimen. The reaction chamber is evacuated through an outlet system so that continuous processing of samples can be achieved.

11 Claims, 1 Drawing Figure

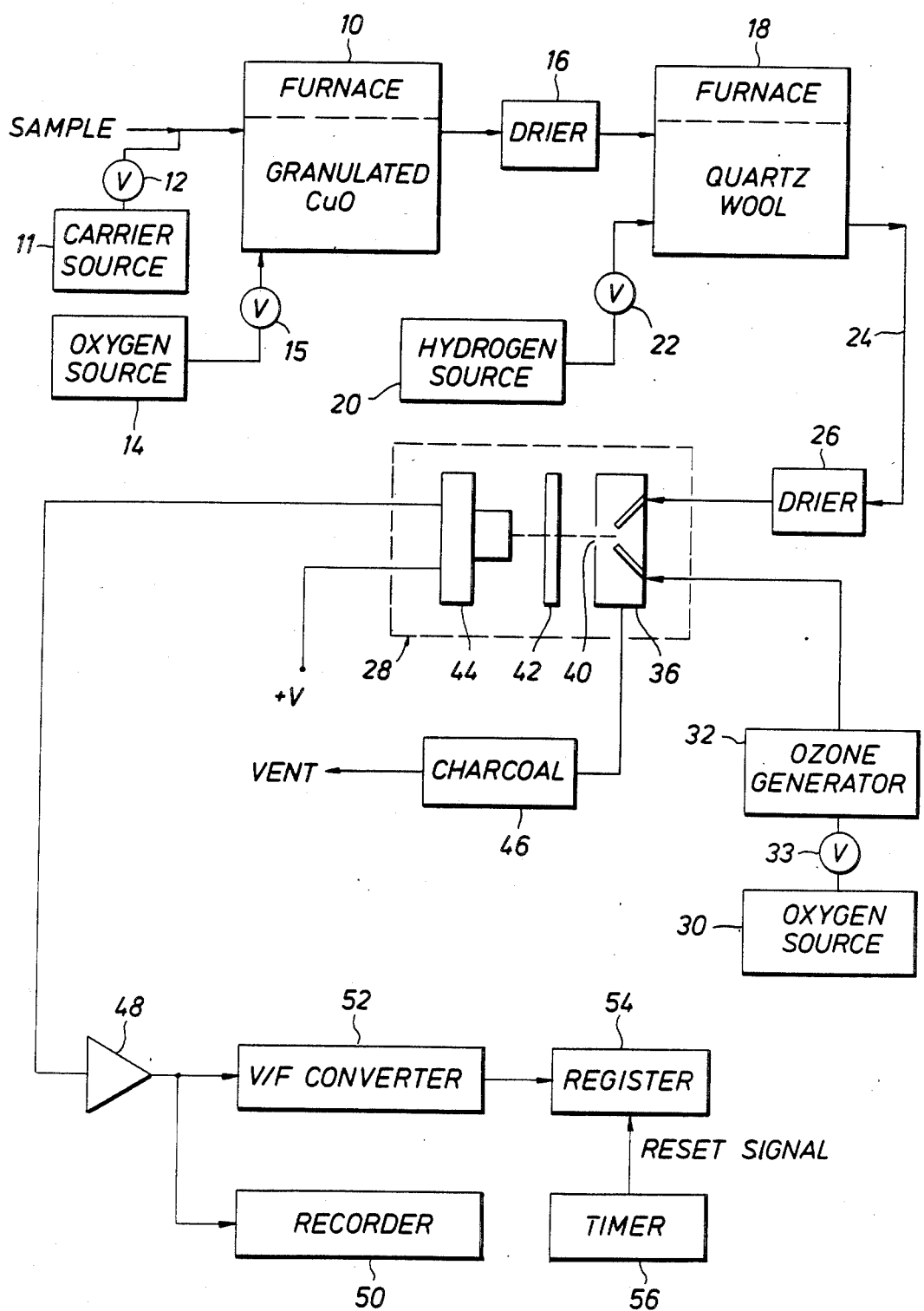

CHEMILUMINESCENT SULFUR DETECTION APPARATUS AND METHOD

RELATED APPLICATION

This application is a division of application Ser. No. 232,891 filed Feb. 9, 1981 subsequently issued as U.S. Pat. No. 4,352,779 on Oct. 5, 1982.

BACKGROUND OF THE DISCLOSURE

This invention is directed to both a method and an apparatus for the detection of chemically bound sulfur. Sulfur which is chemically bound may occur in either organic or inorganic compounds, which are equally susceptible to analysis. Typical compounds include sulfates, sulfides, sulfoxides and sulfites. The output of the apparatus is achieved through an observation of chemiluminescent conversion.

Various procedures for testing for sulfur compounds have been known heretofore. One example is described in U.S. Pat. No. 3,749,929, of Wooten. That disclosure sets forth a chemiluminescent method of detecting three various compounds through a chemiluminescent procedure with atomic oxygen. That disclosure leaves open the problem of sorting out the three compounds. This lack of discrimination is believed to be fatal to this approach.

The patent of Haas, U.S. Pat. No. 3,877,819, sets forth a hydrogen burner capable of detecting phosphorous or sulfur bearing vapors. It is said that chemiluminescence is used, but this appears inconsistent with the description found in that disclosure referencing a flame. More aptly, this appears to be a flame operated analytical process, as opposed to a flameless chemiluminescent reaction.

U.S. Pat. No. 4,097,239 of Patterson discloses a multi-flame approach. Mention is made of a hydrogen rich atmosphere, but, even assuming that this is the case, this disclosure is directed to a flame photometric detection apparatus.

Several techniques exist for detection of sulfur dioxide, and one such disclosure is Neti, U.S. Pat. No. 4,077,774. This process utilizes a reactor to oxidize hydrocarbons and thereafter irradiates the gas output with ultraviolet light to measure the level of fluorescence as a result of the irradiation. Fluorescence measurement is thought to be a more gross phenomena in comparison with chemiluminescence and would appear not to have the dynamic range for trace quantities of the sort which can be detected by this disclosed method. Of lesser significance of the approaches set forth are U.S. Pat. Nos. 3,984,688, 3,973,914, 3,700,896 and 3,838,969.

Without being specific, the procedures disclosed in the references do not appear to have the dynamic range. While specific data indicating the lower limits of their sensitivity is not available, the sensitivity of the presently disclosed procedure is quite surprising, and a wide dynamic range appears available from this disclosed procedure.

BRIEF DESCRIPTION OF THE DISCLOSURE

This disclosure is directed to a chemiluminescent reaction step coupled with a preliminary oxidation and/or hydrogenation step(s). The chemiluminescent conversion step utilizes the reaction of hydrogen sulfide with ozone in a reaction chamber. The reaction with ozone is accompanied by an energy release having the form of photoemission of a quanta of light. This appears to occur as one of the elements reduces its energy state to the ground state which occurs on emission of a quanta of light within a specified wavelength band. The quanta of light so released is represented hereinafter by the symbol "$\epsilon$". This conversion occurs within a reaction chamber, the chamber being constructed with a transparent window to enable a light detector to view the chamber and thereby observe the photoemission which occurs in the chamber. One advantage of the present invention is that quantitation of the sulfur bearing sample occurs through the measure and integration over a period of time sufficient to pass the sample through the apparatus whereby a photomultiplier tube output is integrated and, on application of a suitable scale factor, converted into a measure of sulfur content in the specimen. It appears that the apparatus can measure sulfur contents down in the range of one part per million relatively easily, perhaps even as low as one part per billion. Indications are the device will quantitate upward into the percentage range as well.

Interestingly, the present invention can utilize a sample which is in gas, liquid or solid form. The sample is typically supplied with an inert gas carrier for a first conversion from a sulfur bearing compound and is then exposed to excessive hydrogen to be converted into hydrogen sulfide. This forms the sample into an easily handled compound input to the reaction chamber where the chemiluminescent conversion occurs. Thus, the present invention has the feature that conversion of the sample is readily accomplished to form an easily handled intermediate state. The implementation is made easier by preliminary conversion to hydrogen sulfide. To the extent that excessive hydrogen is comingled with the sample incoming to a conversion chamber, the excess hydrogen, even if it is passed to the reaction chamber, does not oxidize with a chemiluminescent conversion.

SUMMARY OF THE INVENTION

The present invention is directed to a method and apparatus overcoming problems of prior art structures. Briefly, the method steps contemplated include a first conversion step whereby excessive elemental hydrogen is comingled with the specimen to convert it at elevated temperature into hydrogen sulfide. It occurs in the presence of a carrier gas. A preliminary step useful for certain classes of specimen compounds is exposure of the specimen to copper oxide or some other metal oxide having an excess of available bound oxygen to thereby convert a portion or perhaps all of the sample to an oxide of sulfur. It is thereafter converted by hydrogenation, and, after drying, it is introduced into a reaction chamber. The initial step involves oxidation of the sample, drying to remove moisture and thereafter reaction in a hydrogen rich atmosphere. The sulfur bearing sample, presumed to be an organic sulfur compound at the beginning, is thus first converted to some oxide of sulfur, thereafter converted into hydrogen sulfide and is lastly mixed with ozone in a reaction chamber for a reaction resulting in photoemission of measurable energy.

A chemiluminescent detector mechanism comprising a reaction chamber having an inlet for ozone from an ozone generator mixes the ozone with the hydrogen sulfide sample (flowing with a neutral or inert gas), and there is a chemical reaction resulting in photoemission of light energy. In the reaction chamber, a window, preferably including an optical filter, passes light energy in a specified pass band of the approximate range of 300 to 500 nanometers, and this light is applied to a photomultiplier tube or some other light measuring device. The preferred form, being a photomultiplier tube, forms an electrical signal for each quantum of light, and this is integrated as a function of time, stored and thereby represent a measure of the sulfur content of the sample.

The output of the apparatus can be used relatively easily in that an amplifier circuit connected to the light detector forms an output signal which is typically in the form of sharp spikes, peaks or pulses. They are totalled, the sum being incremented for the interval through which measurements are made, and the output is the integrated signal representing the sulfur content of the specimen. This can be readily displayed on a digital counter and quantified through the use of a scale factor to form a digital representation of sulfur content in the sample or specimen. The scale factor may be applied by electronic means to effect direct quantitation.

BRIEF DESCRIPTION OF THE DRAWINGS

The single drawing is a flow chart and schematic diagram illustrating the method and apparatus of the present invention for detection and measurement of sulfur content in a sample.

DETAILED DESCRIPTION OF THE ILLUSTRATED EMBODIMENT

Attention is first directed to the only drawing. The apparatus and method will be described jointly. The description will set forth the mode of operation and will specify the arrangement of apparatus to carry out the present invention. It begins with a sample, the sample having the form of a liquid, gas or solid. In the event that it is a solid, it typically but not necessarily is ground or pulverized. The sample may be an organic or inorganic compound involving sulfur. The sample will be described hereinafter, where necessary, for use in equations with the symbol "RS". The sample "RS" is thus understood to be some type of compound which contains sulfur. The present invention appears to be applicable to all compounds of sulfur. None are known which cannot be analyzed through the use of the present invention. The sample is thus obtained in some specified quantity. A carrier gas 11, typically an inert gas, is also used to initiate the process. The sample is introduced into furnace 10 for immediate contact with carrier gas, which is flow controlled by means of valve 12. Where gases and liquids are involved, a flow rate of about 1 to 100 cubic centimeters per minute is adequate. The carrier gas typically constitutes between ten and ninety-eight percent of the total system flow. It is not critical other than the carrier gas modifies the flow rates occurring through the entire procedure and, in that sense, constitutes a scale factor.

The furnace 10 is filled with granulated copper oxide. Other oxides such as vanadium pentoxide can be used as long as they have the characteristic that they accept oxygen and give it up readily at elevated temperature. Moreover, the granulated copper oxide is ground to particles or flakes so that it has much surface area. An increase in surface area per weight enhances efficiency. However, it is not essential that this be high. It is expedient that the surface area/weight ratio be increased, but not to the extent of causing excessive restriction.

The sample and carrier gas are thus introduced to the furnace 10. They are introduced for a dwell time of a few seconds up to several minutes. The furnace 10 is operated at an elevated temperature range, typically in the bracket of 300° C. to 1100° C. The pressure in the chemiluminescent relation chamber 36, usually is equal to slightly greater than atmospheric pressure; however, vacuum may be applied at the chamber vent to enhance chemiluminescence thereby increasing sensitivity. Chemiluminescence further may be enhanced by closely controlled heat application to the reaction chamber. It is sufficient that the carrier gas be introduced under a relatively low pressure differential to cause the carrier gas and sample to flow through the furnace 10 and to eventually leave the chamber 36. High pressures can be accommodated, but they are not required. The volume of the furnace 10 is relatively small, a typical volume being in the range of about 1.0 liter or less. Larger volumes are not needed. The furnace is preferably temperature stabilized by a thermostat system.

When the sample and carrier gas are introduced, a conversion occurs in the furnace whereby the sulfur bearing sample "RS" is converted to some kind of oxide of sulfur. The conversion need not be complete, but it is preferable that it be substantially complete. There are several oxides of sulfur, and it is not particularly important which oxide of sulfur is obtained.

When the furnace is not in use to process a sample and after it has been used sufficiently that a substantial portion of the oxide in the copper oxide has been depleted, it is appropriate to open a valve 15 and introduce oxygen from an oxygen source 14 into the furnace 10 at an elevated temperature to oxidize the copper oxide to restore it to its original state having an increased amount of oxide. Indeed, pure copper can be originally placed in the furnace, and, through the combination of long term exposure at elevated temperatures, it can be oxidized. This needs to be recharged periodically. The valve 15 is switched off and is normally left closed because recharging with oxygen is not routinely required, and it is done only periodically. It is also feasible and appropriate to meter a very small flow of oxygen, via valve 15, continuously. This offers continuous replenishment of copper oxide and negates the necessity of periodic recharging, however, precautions must be taken not to allow formation of an explosive mixture with hydrogen in the furnace 18.

The carrier gas is introduced at a pressure and flow rate to eventually force the sample from the furnace 10 through a dryer 16. The dryer 16 removes water which is formed in the sample through oxidation. The dried and converted sulfur bearing sample "RS", now in the form of oxides of sulfur, is then introduced to the second furnace 18. This furnace 18 is preferably but not necessarily packed with glass wool, in the form of quartz fibers. They are included to increase surface contact between hydrogen and the introduced sample. A hydrogen source 20 is connected with the furnace 18 through a valve 22. The valve 22 is opened to admit elemental hydrogen to the furnace. The sample is also introduced to the furnace. They are introduced and comingled in the midst of the glass wool which fills the furnace. The glass wool is believed to function not as a catalyst, but simply as a mechanical expedient to increase turbulence in comingling of the two constituents of the furnace, thereby increasing the likelihood of reaction. The reaction which occurs is reduction by hydrogenation. To this end, dwell time in the furnace is preferably sufficiently long that substantially all the sulfur introduced into the furnace is converted, and the conversion is carried out in the presence of the rich hydrogen atmosphere at elevated temperature. This dwell time can range up into a few minutes. Depending on sample size, concentrations, flow rates, temperature and the like, full conversion can be accomplished in just a few seconds. In lieu of glass or quartz wool, a hydrogenation catalyst consisting of one of several noble metals or combination of noble metals—such as nickel, platinum, gold, or silver may be inserted into furnace 18 to encourage hydrogenation and allow operation of the furnace at a lower temperature.

The conversion which occurs in the furnace 18 occurs at an elevated temperature, typically in the range of 300° C. to about 1400° C. After conversion, the hydrogen sulfide and other products of combustion, including some elemental hydrogen, flow out through a line 24. Again, the flow rate through this line is determined in part by the flow rate at which the carrier gas is introduced and the additional flow of hydrogen from the hydrogen source 20. Pressure need not be excessive. Rather, the pressure and flow rate are determined in the main by the upstream flow rates and downstream restrictions.

The carrier gas now supports and conducts hydrogen sulfide in gaseous form. To the extent that water is present, it is removed by passing the gas flow through a drier 26. The drier 26 is preferably similar to the drier 16, the two being water selective removing devices.

The numeral 28 identifies a detection system including several components. As a preliminry to understanding how it operates, it must be first noted that support structure includes an oxygen source 30. The oxygen source delivers, by means of valve 33, oxygen to an ozone generator 32 which, in turn, delivers ozone to the detection means 28. It includes a reaction chamber 36 which is an opaque chamber having a small porthole. The porthole 40 opens to the exterior and is closed over so that light may leave through an optical filter 42. The optical filter 42 allows the appropriate wavelength of emitted light to strike the sensing area of a photomultiplier tube or photodiode 44, hereinafter referred to as a PMT. The chamber 36 receives a flow of ozone from the ozone generator and the sample flowing in the inert carrier gas. It is thus a reaction chamber for chemiluminescent conversion of the hydrogen sulfide introduced into the reaction chamber. It is believed that the conversion which occurs in the chamber is oxidation of the hydrogen sulfide to form metastable sulfur dioxide. The excited sulfur dioxide molecules then relax to the ground state with the liberation of a quanta of light energy having the form of a photoemission. This is passed through the port or window 40, filtered by the optical filter 42 and observed for measurement purposes by the PMT 44.

It appears that the four equations listed below describe in very general form the conversions which occur in the present method. Briefly, the first equation shows the reaction of the chemically bound sulfur compound "RS" with either oxygen or ionized oxygen. The oxygen is present in the furnace 10 in the typical form of a metal oxide. Whatever the form, the first step forms various oxides of sulfur indicated by the appropriate symbol and sum, perhaps a trace of the introduced sulfur compound or a derivative thereof. The second equation sets forth the hydrogenation step which occurs in furnace 18. Various reaction products which may occur are dehydrated by passing through the driers 16 and 26. The third and fourth equations set forth the reaction believed to occur in the reaction chamber 36. The reaction chamber 36 has an outflow through a charcoal filter 46 which is thereafter vented.

$$RS + XO^- + 3O^- = SO_x + CO_2 + H_2O \quad (1)$$

$$SO_x + XH_2 + H_2 = H_2S + XH_2O \quad (2)$$

$$H_2S + O_3 = SO_2^* + H_2O \quad (3)$$

$$SO_2^* = SO_2 + \epsilon \quad (4)$$

The PMT 44 is supplied with a suitable negative voltage for its operation. Ideally it is positioned within a thermally insulated, light-tight and hermetically-sealed chamber for improved stability, sensitivity and endurance. While other photosensitive devices can be used, the PMT 44 is preferably a set of perhaps eight to twelve dynodes which reflect the light falling thereon in the form of enhanced electron flow to form an output signal which has been amplified by many fold, the output signal being supplied to an amplifier 48 or photocounter. The amplifier 48 forms an electrical signal pulse for light perceived by the PMT 44. The electrical signal can be stored on a time base strip chart by a recorder 50. Alternatively, they can be supplied to a voltage-to-frequency convertor 52. This converts the analog output signal from the analog form into a digital procession of pulses supplied to a storage register 54. The register 54 can be reset to a zero value, thereafter permitted to run and store a number of pulses indicative of the amplitude of the signal recorded from the specimen.

Operation of the apparatus follows the procedure set forth above. In particular, certain variables in its operation should be noted. As a general premise, the oxygen sources 14 and 30 flow oxygen of a fairly pure form (ninety-eight percent or better, except that inert gases comingled with the oxygen are no problem), and they flow through corresponding valves 15 and 33 at regulated rates. To the extent that excess oxygen is introduced, no particular problem arises from the excess. A portion of it is formed into ozone by the ozone generator 32. The ozone rapidly combines with the hydrogen sulfide to assure that the chemiluminescence phenomenon does occur and that the quanta of light are emitted.

The optical filter 42 might be obscured by omission of the drier 26. This results from a combination of factors which form condensation on the optical filter 42. To this end, the amount of water in the gas which is introduced to the reaction chamber 36 is reduced so that condensation does not form and thereby quench the photoemissions which pass through the optical filter 42.

As will be understood, the apparatus shown in the single drawing can be obtained from alternate sources, but the preferred source of the equipment is Antek Instruments, Inc. The voltage-to-frequency convertor register and electrometer can also be obtained from Antek Instruments, Inc.

While the foregoing is directed to the preferred embodiment, the scope thereof is determined by the claims which follow:

I claim:

1. A method for determining the total chemically combined sulfur in a specimen which comprises the steps of:
   (a) introducing the specimen in the presence of a carrier gas into a furnace operated at an elevated temperature above 300° C. into the presence of a metal oxide to convert at least a portion of the chemically bound sulfur into oxides of sulfur;

(b) thereafter passing the specimen from the furnace through a dryer to remove at least a portion of the water therein;

(c) after water removal, exposing the specimen to a hydrogen rich atmosphere within a furnace at an elevated temperature to convert the specimen including chemically combined sulfur into hydrogen sulfide;

(d) exposing the hydrogen sulfide produced from step (c) to ozone to form a chemiluminescent reaction; and (e) measuring the magnitude of the chemiluminescent reaction by observing quanta of light to obtain the quantity of chemically combined sulfur in the specimen.

2. The method of claim 1 wherein the chemiluminescent reaction is observed within the range of about 300 to 500 nanometers.

3. The method of claim 1 including the step of converting elemental oxygen into ozone by passing it through an ozone generator.

4. The method of claim 1 including the step of drying the hydrogen sulfide obtained from step (c) to reduce the water content therein below a specified level.

5. The method of claim 1 including the step of optically filtering the chemiluminescent reaction quanta of light in a specified optical range.

6. The method of claim 1 including the method step of integrating over a period of time the measured optical output from the chemiluminescent reaction, the integration being accomplished by first converting a signal representative thereof into digital signals.

7. The method of claim 1 wherein the hydrogen rich atmosphere is substantially devoid of free oxygen.

8. The method of claim 1:

(f) and further including a step of drying the hydrogen sulfide obtained from step (c) to reduce the water below a specified level; and (g) and further wherein the hydrogen of step (c) is diatomic hydrogen and the specimen is comingled with the diatomic hydrogen in the furnace, and wherein the elevated temperature is between 300° to 1200° C.

9. The method of claim 1 wherein the metal oxide is a catalyst for the sulfur conversion.

10. The method of claim 1 wherein the metal oxide is copper oxide or vanadium pentoxide.

11. The method of claim 1 wherein the hydrogen of step (c) is diatomic hydrogen and the specimen is comingled with the diatomic hydrogen in the furnace, and wherein the elevated temperature is maintained between 300° to 1200° C. to substantially convert al the chemically bound sulfur in the specimen to hydrogen sulfide.

* * * * *